United States Patent [19]

Freeman

[11] Patent Number: 5,193,537
[45] Date of Patent: Mar. 16, 1993

[54] METHOD AND APPARATUS FOR TRANSCUTANEOUS ELECTRICAL CARDIAC PACING

[75] Inventor: Gary A. Freeman, Newton Center, Mass.

[73] Assignee: ZMD Corporation, Wilmington, Del.

[21] Appl. No.: 536,968

[22] Filed: Jun. 12, 1990

[51] Int. Cl.⁵ .......................................... A61N 1/362
[52] U.S. Cl. .............................. 128/419 PG; 128/421
[58] Field of Search ............. 128/419 PG, 419 D, 421

[56] References Cited

U.S. PATENT DOCUMENTS

| | | | |
|---|---|---|---|
| 2,558,270 | 6/1951 | Reiter | 128/428 |
| 2,590,876 | 4/1952 | Landauer | 128/417 |
| 2,771,554 | 11/1956 | Gratzl | 250/27 |
| 2,864,371 | 12/1958 | Parodi | 128/415 |
| 2,915,066 | 12/1959 | Parodi | 128/419 |
| 3,024,783 | 3/1962 | Timcke | 128/2 |
| 3,050,695 | 8/1962 | Du Vall | 331/52 |
| 3,077,884 | 2/1963 | Batrow et al. | 123/423 |
| 3,645,267 | 2/1972 | Hagfors | 128/421 |
| 3,731,111 | 5/1973 | Charters | 307/106 |
| 3,817,254 | 6/1974 | Maurer | 128/421 |
| 3,888,261 | 6/1975 | Maurer | 128/420 |
| 4,014,347 | 3/1977 | Halleck et al. | 128/422 |
| 4,147,171 | 4/1979 | Greene et al. | 128/421 |
| 4,177,817 | 12/1979 | Bevilacqua | 128/802 |
| 4,210,151 | 7/1980 | Keller, Jr. | 128/421 |
| 4,222,386 | 9/1980 | Smolnikov et al. | 128/419 PG |
| 4,237,899 | 12/1980 | Hagfors et al. | 128/422 |
| 4,331,157 | 5/1982 | Keller, Jr. et al. | 128/419 |
| 4,349,030 | 9/1982 | Belgard et al. | 128/419 |
| 4,580,570 | 4/1986 | Sarrell et al. | 128/421 |
| 4,723,536 | 2/1988 | Rauscher et al. | 128/1.5 |
| 4,787,389 | 11/1988 | Tarjan | 128/419 D |

FOREIGN PATENT DOCUMENTS 0314078  3/1989  European Pat. Off. .
1350016  4/1974  United Kingdom .

OTHER PUBLICATIONS

"Cardiac Arrest and Ventricular Fibrillation," McMillan, I. K. R., et al., J. Thorax, vol. VII, 1952.
Physiology & Biophysics, Theodore C. Ruch, Ph.D & Harry D. Patton, Ph.D., M.D., W. A. Saunders Company, Philadelphia and London, 1964.
"Clinical experience and problems encountered with an implantable pacemaker," Morris, J. D. et al., J. Thoracic Cardiovascular Surgery, vol. 50, No. 1, 1965.
Control of Heart Action by electrical and Mechanical Means, Paul M. Zoll & Arthur J. Linenthal, Year Book Medical Publishers, Inc., Chicago, Sep. 1966.
"Measurement of the pain threshold determined by electrical stimulation and its clinical application" Notermans, S. L. H., Neurology, pp. 1071-1086, 1966.
Cardiac Pacemakers, H. Siddons & E. Sowton, Charles C. Thomas, Springfield, 1967.
Principles of Applied Biomedical Instrumentation, L. A. Geddes & L. E. Baker, John Wiley & Sons, New York, London, 1968.
"Historical Development of Cardiac Pacing," Paul Zoll, MCV/Q, vol. 7, No. 4, 1971.
Electrogenesis and Contractility in Skeletal Muscle Cells, Jozef Zachar, Publishing House of the Slovak Academy of Sciences, Bratislava, 1971.
"The Response of Human Motor Nerve," W. G. S. Stephens, P.R.S.E., vol. 70, B, pp. 49-61 1966-67.
Abstracts, The Journal of Emergency Medicine, vol. 6, No. 1, pp. 79-83, 1988.

(List continued on next page.)

Primary Examiner—William E. Kamm
Assistant Examiner—Scott M. Getzow
Attorney, Agent, or Firm—Fish & Richardson

[57] ABSTRACT

Method and apparatus for transcutaneously pacing the heart with pacing stimuli each of which comprise a series of individual pulses. The heart reacts to the series of pulses as if the series were one continuous pulse, whereas the pulse series produces skeletal muscle reactions that are similar to that which would be expected for individual pulses. The result is reduced stimulation of skeletal muscles and nerves, and less discomfort for the patient. Further reduction in stimulation of skeletal muscles and nerves can be achieved by providing a series of subthreshold initial pulses in each pacing stimulus.

30 Claims, 4 Drawing Sheets

OTHER PUBLICATIONS

"Improving Pacemaker Electrodes", Cardiac Pacing: Proceedings of the IVth International Symposium On Cardiac Pacing", H. J. Thalen, Ed., 1973.

"Transcutaneous Nerve Stimulation for Control of Pain," C. Norman Shealy et al., Surg. Neurol., vol. 2, Jan. 1974.

"Optimal Stimulus Parameters for Minimum Pain in the Chronic Stimulation of Innervated Muscle," F. Gracanin et al., Arch. Phys. Med. Rehabil., vol. 56, Jun. 1975.

"Pacemaking and Ventricular Fibrilation," M. Jones, B. S. and L. A. Geddes, M. E., Ph.D, Cardiovascular Research Bulletin, vol. 15, No. 4, 1977.

Impedance Measurements in Biological Cells, Otto F. Schanne & Elena Ruiz P.–Ceretti, A Wiley-Interscience Publication, John Wiley & Sons, New York, 1977.

"Comparative efficacy of damped sine wave and square wave current for transchest ventricular defibrillation in animals", J. D. Bourland et al., Medical Instrumentation, vol. 12, No. 1, 1978.

"Tissue stimulation: theoretical considerations and practical applications," L. A. Geddes & J. D. Bourland, Med. & Biol. Eng. & Comput., vol. 23, No. 2, pp. 131–137, 1985.

"Choice of the Optimum Pulse Duration for Precordial Cardiac Pacing: A Theoretical Study," L. A. Geddes, et al., Pace, vol. 8, 1985.

"Transcutaneous Electrical Nerve Stimulators," American National Standard, Association for the Advancement of Medical Instrumentation, 1986.

TextBook of Medical Physiology, Arthur C. Guyton, M.D., W. B. Saunders Company, 1980.

"Symmetrical Biphasic TENS Waveform for Treatment of Back Pain", Jerry Lampe and Bill Dunn, The Clincal Journal of Pain, vol. 3, No. 3, 1987.

"Minimizing Cutaneous Pain During Electrical Stimulation," IEEE: 9th Annual Conference of The Engineering in Medicine and Biology Society, IEEE 1987.

"Suggested Electrode Placement Patterns Using Nuwave and Lo-back Electrodes," Staodyn, Inc., 1988.

Computerized EMG Monitoring in Anesthesia And Intensive Care, Harvey L. Edmonds, Jr. Ph.D., et al., Instrumentation Science Foundation, Malherbe Publishing Corp., the Netherlands, 1988.

"Modified impulse diminishes discomfort of transcranial electrical stimulation of the motor cortex," Josef Zentner et al., Electromygr. Clin. Neurophysiol., 29, pp. 93–97, 1989.

"A Comparative Study of Five Transcutaneous Pacing Devices in Unanesthetized Human Volunteers," Michael B. Heller, MD et al., Prehospital and Disaster Medicine, Jul.–Sep., 1989.

Goovaerts et al., "A General-Purpose Microprocessor System for Medical Instrumentation and Electrical Stimulation", J. Biomed Eng., vol. 6, pp. 90–96 (Apr. 1984).

Geddes, "A Short History of the Electrical Stimulation of Excitable Tissue Including Electrotherapeutic Applications", Supp. to The Physiologist, vol. 27, No. 1 (Feb. 1984).

Eriksson et al., "Hazard From Transcutaneous Nerve Stimulation In Patients With Pacemakers", The Lancet, p. 1319 (Jun. 17, 1978).

Geddes et al., "Electroventilation", American Journal of Emergency Medicine, vol. 3, No. 4, pp. 338–339 (Jul. 1985).

Rosenbaum et al., "Simple Cardiac Pacemaker and Defibrillator", The Journal of American Medical Association, vol. 155, No. 13, p. 1151 (1954).

Schechter, "Background of Clinical Cardiac Electrostimulation; IV. Early studies on feasibility of accelerating heart rate by means of electricity", New York State Journal of Medicine, pp. 395–404, Feb. 1, 1972.

Kahn et al., "Technical Aspects of Electrical Stimulation Devices", Med. Progr. Technol., vol. 1, No. 2, pp. 58–68 (1972).

Schechter, "Background of Clinical Cardiac Electrostimulation; III. Electrical regulation of rapid cardiac dysrhythmias", New York State Journal of Medicine, pp. 270–284, Jan. 15, 1972.

Schechter, "Background of Clinical Cardiac Electrostimulation; VII. Modern era of artificial cardiac pacemakers", New York State Journal of Medicine, pp. 1166–1190, May 15, 1972.

Goovaerts et al., "A Programmable Stimulator for Physiological Applications", Medical and Biomedical Engineering, pp. 112–118 (Jan. 1975).

Furman et al., Pulse Duration Variation and Electrode Size as Factors in Pacemaker Longevity", The Journal of Thoracic and Cardiovascular Surgery, vol. 69, No. 3, pp. 382–389 (Mar. 1975).

Fisher et al., "Termination of Ventricular Tachycardia With Bursts of Rapid Ventricular Pacing", The American Journal of Cardiology, vol. 41, pp. 94–102 (Jan. 1978).
"A New Approach to Pain", reprinted from Emergency Medicine (Mar. 1974).
Ritchie et al., "A Simple Variable 'Square-Wave' Stimulator for Biological Work", vol. 21, pp. 64–65 (Apr. 1944).
Schechter, "Background of Clinical Cardiac Electrostimulation; VI. Precursor apparatus and events to the electrical treatment of complete heart block", New York State Journal of Medicine, pp. 953–961, Apr. 15, 1972.
Stimulation Technology, Inc., Minneapolis, MN, EPC® Stimulators Brochure.
Cotter, "Overview of Transcutaneous Electrical Nerve Stimulation for Treatment of Acute Postoperative Pain", Medical Instrumentation, vol. 17, No. 4, pp. 289–292 (1983).
Pearce et al., "Myocardial Stimulation with Ultrashort Duration Current Pulses", PACE, vol. 5, pp. 52–58 (1982).
Geddes, "The Beginnings of Electromedicine", IEEE Engineering in Medicine and Biology Magazine, pp. 8–23 (Dec. 1984).
Castillo et al., "Use of Electrical Pacemakers in the Management of Cardiac Arrhythmias", Geriatrics, pp. 117–131.
Tursky et al., "Electrocutaneous Threshold Changes Produced By Electric Shock", Psychophysiology, vol. 7, No. 3, pp. 490–498 (1971).
Hill et al., "Relationship of Electrically Induced Pain to the Amperage and the Wattage of Shock Stimuli," *Wattage, Amperage and Pain Stimuli*, pp. 464–472 (1952).
W. G. S. Stephens, "The Response of Human Motor Nerve", P.R.S.E., vol. LXX, B, pp. 49–61 (1966–1967).
Cook, "Effects of Low frequency stimulation on the monosynaptic reflex (H reflex) in man", Neurology, vol. 18, pp. 47–51 (1968).
Jeneskog, "Cutaneous inhibition of high threshold muscle afferent pathways", Acta Physiol Scan, 107: 297–308 (1979).

METHOD AND APPARATUS FOR TRANSCUTANEOUS ELECTRICAL CARDIAC PACING

BACKGROUND OF THE INVENTION

This invention relates to electrically pacing the heart transcutaneously.

During transcutaneous, or external, electrical pacing of a patient's heart, electrical stimuli travel from the pacing apparatus' electrodes to the heart through the patient's skin and skeletal thorax muscles to stimulate the heart. Depending on the magnitude of the stimuli and the characteristics of a particular patient's skeletal muscles, the skeletal muscles may contract in response to the passage of the electrical stimuli through them. Similarly, the passage of the electrical pacing stimuli through the patient's skin may stimulate cutaneous nerves and muscles located near to the skin. This nerve stimulation and skeletal muscle contraction may feel uncomfortable to the patient, or even become painful enough to result in the patient's intolerance of extended transcutaneous heart pacing.

It has been shown (U.S. Pat. No. 4,349,030) that the skeletal muscle contractions and cutaneous nerve stimulation associated with conventional transcutaneous heart pacing may be reduced by lengthening the duration of electrical pacing stimuli to greater than five milliseconds.

SUMMARY OF THE INVENTION

In a first aspect, the invention features pacing stimuli each of which comprises a series of pulses. Each of the pulses is, by itself, incapable of causing a cardiac muscle contraction, but the series of pulses making up each pacing stimulus is capable, as a group, of causing such a contraction. The series of pulses tends to produce less skeletal muscle stimulation than a continuous pulse, thus making extended transcutaneous pacing more bearable for a patient. In preferred embodiments, each pulse averages less than 0.5 msec (preferably less than 250 microseconds, and more preferably less than 50 microseconds); the duty cycle of the pulses (i.e., the percentage of time the pulse is on) is at least 20%, and more preferably at least 50%; and the amplitude of the pacing stimulus in the brief intervals between each pulse is below the minimum amplitude required for skeletal muscle stimulation if one were using a continuous pulse of the same duration as the pulse train (and is preferably substantially zero).

In a second aspect, the invention features reducing skeletal muscle stimulation during pacing by including in the pacing stimuli one or more pulses that have amplitudes below the threshold for skeletal muscle stimulation. Stimulation threshold is here defined as the minimum pulse amplitude required for stimulation if the pulse amplitude of a given pulse train remained constant for the duration of the pulse train. The subthreshold pulses tend to reduce the reaction of skeletal muscles to the above-threshold stimulus that follows them. In preferred embodiments, these subthreshold pulses are the initial pulses in a pacing stimulus itself comprising a series of pulses; the pacing stimulus extends for at least 5 msec (more preferably, at least 40 msec); and some, possibly all, of the subthreshold pulses, and possibly some of the above-threshold pulses, each has an amplitude that is greater than the amplitudes of the preceding pulses in the pacing stimulus.

The reduction in skeletal muscle stimulation is believed to result because the cardiac muscle reacts to the train of pulses as if it were one continuous pulse, whereas at least some of the skeletal muscles react in a manner more akin to the way they would react to individual pulses. It is believed that this difference may result from a filtering of the pulse train as it passes through the chest wall, with the result that the cardiac muscle sees a continuous stimulus, whereas at least some of the skeletal muscles are exposed to the unfiltered, or less filtered, pulses, which, because of their short duration, produce less skeletal muscle stimulation. But whatever physiological actions are actually responsible, the result is that, at cardiac threshold (i.e. at a stimulus amplitude just high enough to cause cardiac contraction), the skeletal muscles are stimulated less by a train of pulses than by a continuous pulse.

Other features and advantages of the invention will be apparent from the following description of a preferred embodiment and from the claims.

DESCRIPTION OF THE PREFERRED EMBODIMENT

Figure 1:
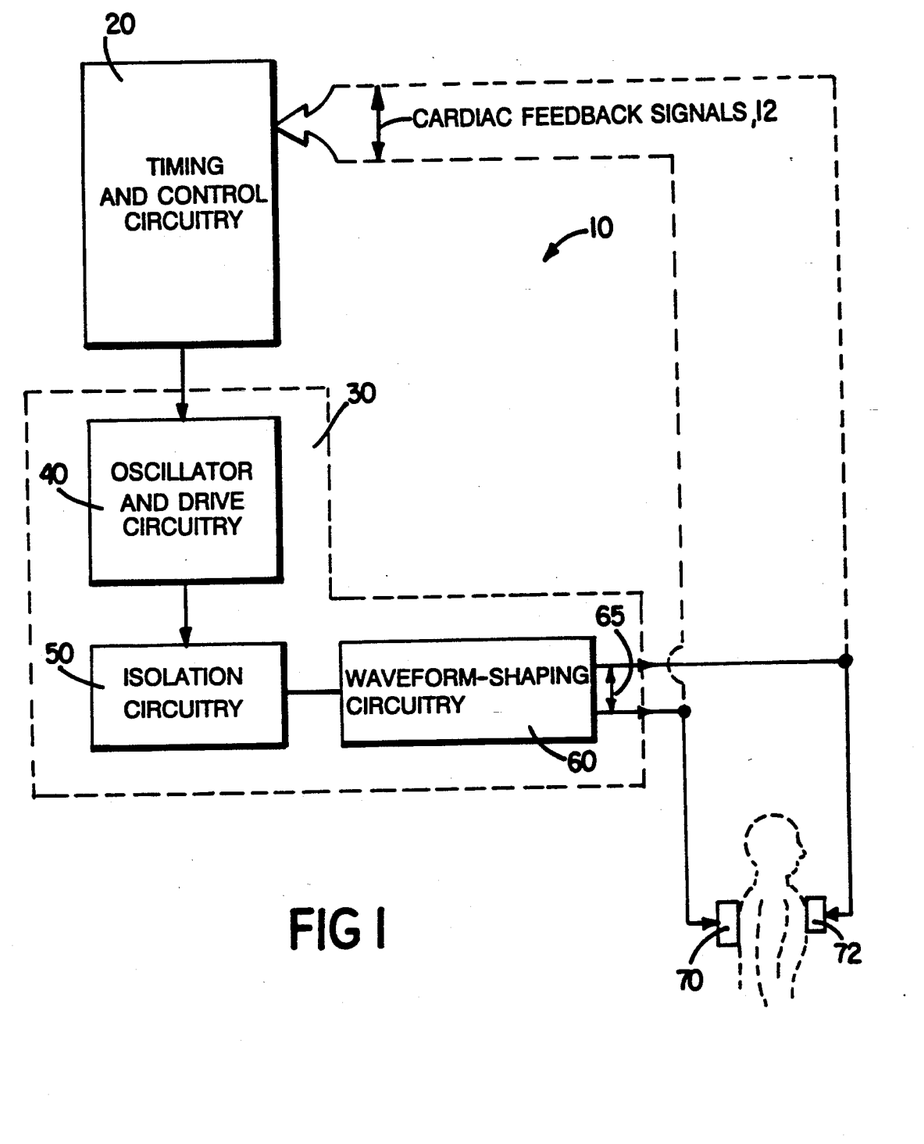
FIG. 1 is a block diagram of a pacing stimuli signal generator according to one embodiment of the invention.

Referring to FIG. 1, there is shown a signal generator 10 for generating electrical pacing stimuli 65 which are to be applied transcutaneously to a patient's heart. The signal generator's timing and control circuitry 20 can accept cardiac feedback signals 12 from the patient to initiate electrical pacing stimuli, or it can operate without such feedback (asynchronous pacing). The timing and control circuitry also sets the timing characteristics of the pacing stimuli, as discussed below. The timing and control circuitry 20 initiates the pacing stimuli by signaling the stimuli generating circuitry 30, which includes oscillator and drive circuitry 40, isolation circuitry 50, and waveform-shaping circuitry 60. Oscillator and drive circuitry 40 generates a stream of pulses that are processed by isolation circuitry 50, which isolates the signal generator's internal voltages from the patient, thereby providing electrical hazard protection for the patient during the patient's exposure to the pacing stimuli 65.

Waveform-shaping circuitry 60 receives the isolation circuitry's pulse stream output and modifies signal characteristics of the pulse stream, e.g., pulse shape, polarity, and amplitude, to generate pacing stimuli 65 having user-specified signal parameters. At the signal generator's output, the pacing stimuli 65 are coupled to posterior and anterior electrodes 70, 72, which together externally deliver the electrical stimuli to the patient for transcutaneous pacing of the patient's heart.

Figure 2A:
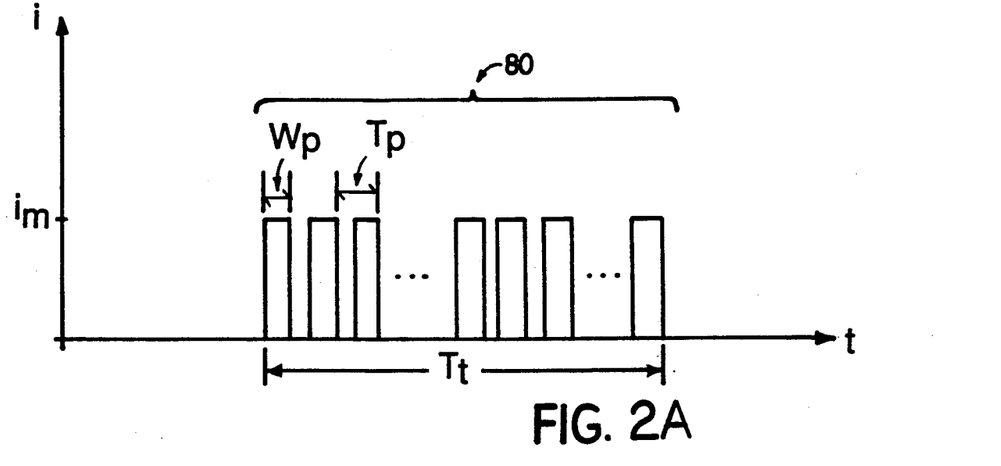
FIGS. 2A and 2B are illustrative examples of electrical pacing stimuli produced by the signal generator of FIG. 1.

Referring to FIG. 2A, the signal generator's electrical pacing stimuli output 65 is composed of pacing pulse trains 80 delivered to the patient to stimulate the patient's heart. The stimuli provide effective transcutaneous stimulation of the heart with reduced patient discomfort from skeletal muscle contraction. The pacing pulse trains 80 each consist of a series of pulses, with each pulse having a time duration, or width, $W_p$, which may be different than the duration of the other pulses in the series.

Figure 2B:
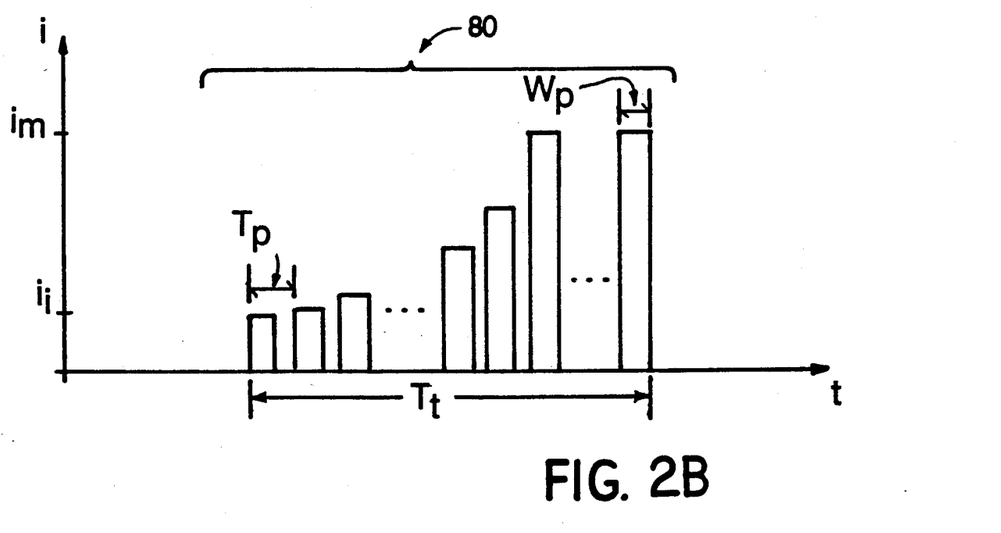
Figure 3:
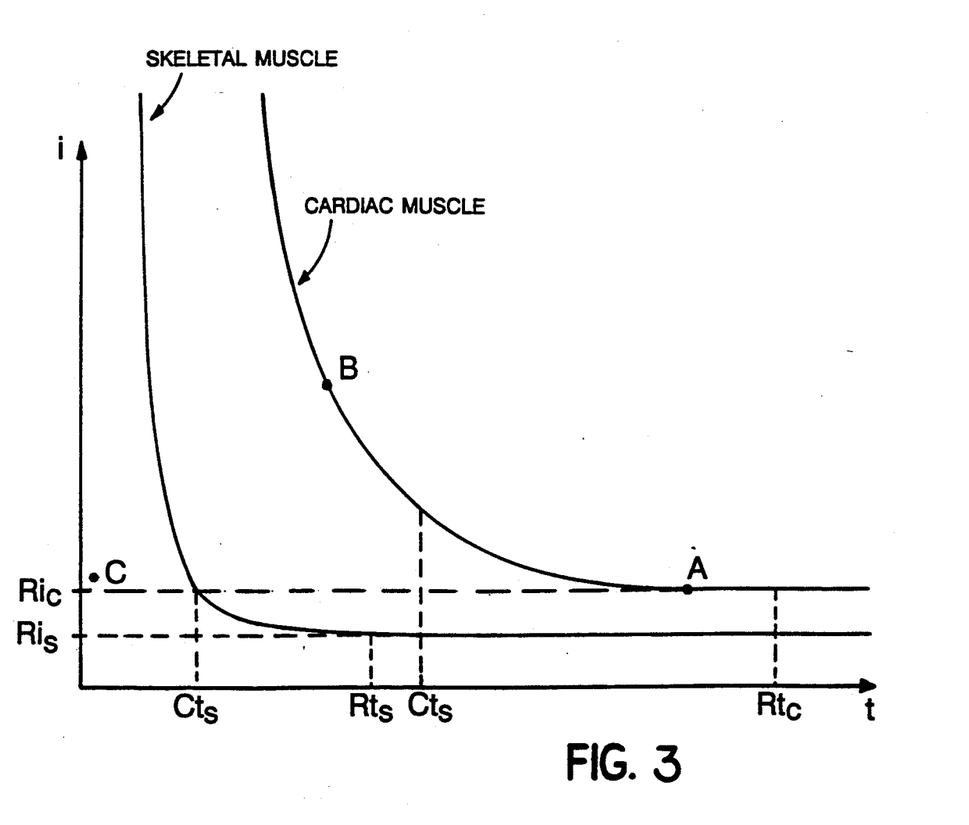
FIG. 3 are plotted characteristics, one for cardiac muscle and one for skeletal muscle, relating a stimulating pulse's strength with the pulse's duration.

Referring also to FIG. 3, there are shown characteristic curves for pulse stimuli, representing the relationship between a pulse's current amplitude, or strength, i, and a pulse's duration, t, for stimulating cardiac muscle and skeletal muscle. The duration, $T_t$, of each pacing pulse train 80 (FIG. 2) is chosen by considering these strength-duration curves. Each curve delineates the minimum duration, t, which an electrical pulse stimulus having a given current amplitude, i, will require to stimulate a muscle. Stated another way, given a pulse amplitude, i, a muscle will not be stimulated unless the pulse duration, t, is on, or to the right of, the corresponding curve. Two different stimulus points lying on the strength-duration curve for a muscle, like points A and B on the cardiac muscle curve, will equally effectively stimulate that muscle.

A minimum pulse amplitude, or rheobase ($Ri_c$ for cardiac muscle and $Ri_s$ for skeletal muscle), defines the smallest pulse amplitude that will stimulate a muscle. Any stimulus having a current amplitude less than the rheobase will not stimulate a muscle, even if the pulse's duration is greater than the rheobase duration, called the utilization time, ($Rt_c$ for cardiac muscle and $Rt_s$ for skeletal muscle). Comparing the strength-duration curves of FIG. 3, the cardiac muscle's utilization time, $Rt_c$, which is greater than approximately 40 msec, is longer than that of skeletal muscle, having a utilization time $Rt_s$ which is considerably less than 40 msec.

Given these utilization times for cardiac and skeletal muscle, a preferable range for the pacing pulse trains' durations $T_t$ is selected with the following consideration. While any stimulus point on the cardiac strength-duration curve produces effective cardiac stimulation, stimulus points having lower current amplitudes tend to produce lower skeletal muscle stimulation than stimulus points having higher current amplitudes, for a given stimulus duration. Accordingly, a pulse stimulus having the characteristics of point A (close to the cardiac utilization time $Rt_c$) stimulates skeletal muscle less than a pulse stimulus having the characteristics of point B, but will stimulate the heart equally effectively. Therefore, by choosing a pulse train duration around the same duration as the cardiac utilization time, the heart can be adequately stimulated by the pulse train while producing less skeletal muscle stimulation than would be produced by a pulse train of shorter duration and correspondingly higher pulse current amplitudes. The total time duration, $T_t$, of each pacing pulse train is therefore preferably at least 5 msec, or more preferably 20 msec, but may be of any duration sufficient to stimulate the heart. The maximum preferable pacing pulse train duration is limited to approximately 150 msec because of safety considerations for inducing cardiac fibrillation.

The pulse width $W_p$ and pulse period $T_p$ of each of the pulses in the pacing pulse trains are also selected based on a comparison of the strength-duration relationships for cardiac muscle and skeletal muscle (FIG. 3). As shown in FIG. 3, a minimum pulse duration, called the chronaxie ($Ct_c$ for cardiac muscle and $Ct_s$ for skeletal muscle), is the pulse duration corresponding to a stimulating pulse amplitude equal to twice the rheobase of a muscle. With a pulse stimulus having a duration shorter than the chronaxie, it becomes increasingly difficult to stimulate a corresponding muscle.

Considering the strength-duration curves of FIG. 3, the cardiac muscle's chronaxie $Ct_c$ is approximately equal to 2 msec and the skeletal muscle's chronaxie $Ct_s$ is approximately equal to 0.5 msec. A pulse stimulus of a duration shorter than the skeletal muscle chronaxie $Ct_s$, having, e.g., the duration of a pulse at point C, would therefore tend not to stimulate either cardiac muscle or skeletal muscle. However, a train of such pulses having suitably adjusted amplitudes and a pulse train duration $T_t$ which is longer than the cardiac muscle chronaxie $Ct_c$, e.g., the stimulus duration of point A, effectively stimulates the heart as if the pulse trains had been filtered by, e.g., the skeletal muscles, to produce a continuous pacing pulse.

Referring again to FIG. 2, based on this consideration, the pulse width $W_p$ of each of the pacing pulses is selected to be less, preferably much less, than the skeletal muscle chronaxie $Ct_s$ (0.5 msec). With pulses of such width, the skeletal muscles tend to be stimulated less than they would if the pacing pulse were a single continuous pulse, but the heart is stimulated as effectively as a continuous pulse. The pacing pulse width $W_p$ for achieving this condition is preferably less than 100 microseconds, and most preferably less than 15 microseconds. Pulse widths of less than about 7 microseconds may produce a pacing pulse frequency which is high enough to cause tissue damage, and thus may need to be avoided. Given the selected pulse width $W_p$, the pacing pulse period $T_p$ is selected to ensure adequate pacing stimulation, or capture, of the heart. The preferred pacing pulse duty cycle is 66%, but a lower duty cycle, e.g., 20%, or a variable duty cycle may be used, provided the given duty cycle is adequate to capture the heart. Generally speaking, the higher the duty cycle, the higher will be the effective filtered amplitude of the continuous pulse that influences the cardiac muscle.

A variation in the form of the pacing stimuli is shown in FIG. 2B. The amplitude, $i_i$, of the first pulse in each pacing pulse train has a subthreshold amplitude, i.e., the amplitude is below the minimum current required for skeletal muscle stimulation if one were using a constant pulse of the same duration as the pulse train. Each of the pulses following the initial pulse has an amplitude greater than that of the previous pulses, with some number of trailing pulses all having a maximum current amplitude, $i_M$. The value of this maximum current amplitude $i_M$ is selected, along with other pulse train characteristics, e.g., pulse train duration, to ensure capture of the heart. For example, a pulse train with a given number of pulses having a maximum current amplitude $i_M$ may require a shorter duration to capture the heart than a pulse train with fewer pulses having a maximum current amplitude greater than $i_M$.

The use of initial, subthreshold pulses, followed by a series of pulses each having an amplitude that is greater than the amplitudes of the preceding pulses is intended to induce accommodation of the skeletal muscles to the pacing pulse train stimuli. Accommodation of a muscle is a physiological phenomenon which can be induced by gradually, rather than abruptly, exposing a muscle to a stimulus amplitude, whereby the stimulating threshold of the muscle is increased beyond the magnitude of the applied stimulus. An accommodated muscle or nerve requires a higher than normal stimulus magnitude to be effectively stimulated, and may even reject stimulation altogether for any magnitude of stimulus increase.

Given the physiological differences between cardiac muscle and skeletal muscle, the amplitudes of the pulses in the pacing pulse train are selected to cause accommodation of skeletal muscles but not to cause accommodation of cardiac muscle. By simultaneously achieving these conditions, the pacing pulse trains effectively stimulate the heart but tend to decrease the skeletal muscle stimulation typically associated with the transcutaneous cardiac muscle stimulation.

While effectively stimulating the heart with decreased skeletal muscle stimulation, the pacing pulse trains also appear to decrease the cutaneous nerve stimulation associated with transcutaneous cardiac pacing. Because the skeletal muscles and cutaneous nerves have similar chronaxies (FIG. 3), the cutaneous nerves, like skeletal muscles, tend to be stimulated less by the pulses in the pacing pulse trains than they would if the pacing pulse were a single continuous pulse.

Referring again to FIG. 1, the signal generator's waveform-shaping circuitry 60 modifies the stream of pulses generated by the oscillator circuitry 40 to create the pacing pulse trains in the pacing stimuli 65. The timing and control circuitry 20 provides further fine adjustment of the pacing pulse train characteristics, for example, pulse shape. Both the waveform-shaping circuitry 60 and the timing and control circuitry 20 may be programmed to include or omit any or more of the pacing pulse train signal characteristics discussed above.

A variety of electrode structures may be used to deliver the pacing stimuli. The pacing stimuli are passed through the patient's thorax from the posterior electrode to the anterior electrode. In view of the reduced skeletal muscle and cutaneous nerve stimulation that is achieved by the pacing stimuli, the contribution of the electrode configuration to stimulation reduction may be less important. Thus, conventional noninvasive pacing electrodes with nonmetallic skin-contacting members, such as those disclosed in U.S. Pat. No. 4,349,030, or as sold by R-2, of Morton Grove, Ill., Physio-Control Corporation, of Redmond, Wash., or ZMI Corporation, of Woburn, Mass., are suitable for delivering the pacing pulse trains. Alternatively, electrodes having metallic skin-contacting members may be adapted to deliver the pacing stimuli.

Figure 4A:
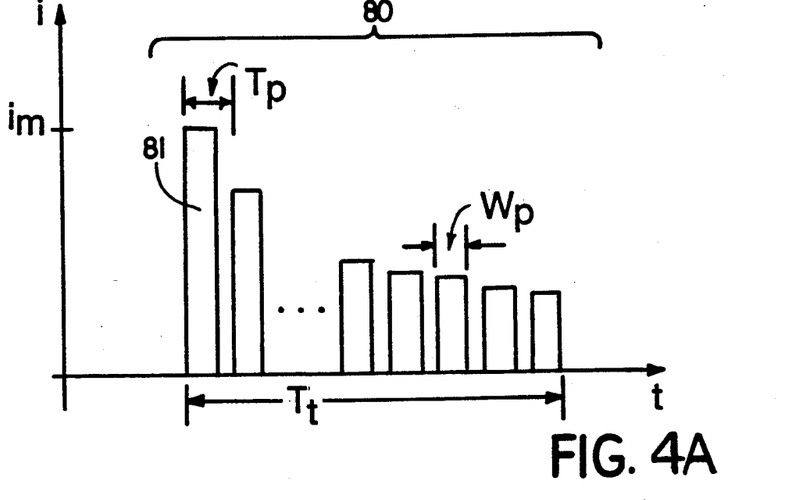
FIGS. 4A-4C are three illustrative examples of alternative pacing stimuli produced by the signal generator of FIG. 1.
Figure 4B:
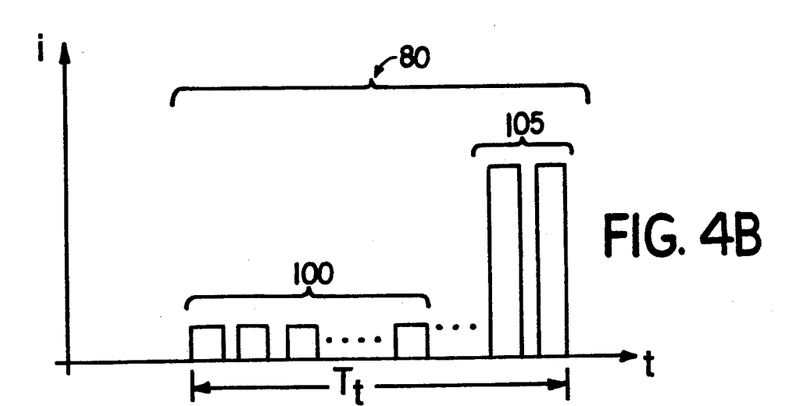
Figure 4C:
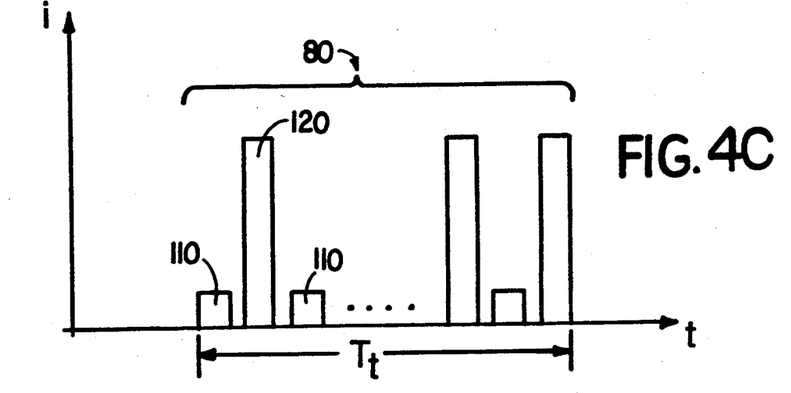

Other embodiments of the invention are within the claims. For example, referring to FIG. 4A, the pacing pulse train could have an initial pulse 81 with a maximum amplitude $i_M$, followed by a series of pulses which each has an amplitude that is less than the amplitudes of all preceding pulses. As shown in FIG. 4B, the pacing pulse train could have an initial portion 100 of subthreshold pulses, all of an equal amplitude, followed by a portion 105 of above-threshold pulses, all of an equal amplitude. The initial portion 100 of subthreshold pulses may include a second portion of subthreshold pulses, all of a second, equal amplitude. Alternatively, as shown in FIG. 4C, the pacing pulse train could have alternating subthreshold pulses 110 and above threshold pulses 120. Another variation for achieving the subthreshold pulses is to vary the duration of the pulses, using shorter durations for the subthreshold pulses, and longer durations for the above-threshold pulses. Given any pulse combination in a pacing pulse train, the pulses in a train could have non-rectangular shapes, e.g., triangular, exponential, or rounded. The duty cycle and duration of pulses can be varied within the pulse train (e.g., there could be brief gaps in the sequence of pulses). Background stimulation (e.g., a train of subthreshold pulses) could be superimposed continuously or just in the intervals between pacing stimuli to further reduce discomfort (as disclosed in my copending application entitled Method and Apparatus for Transcutaneous Electrical Cardiac Pacing with Background Stimulation, filed on even date herewith, and hereby incorporated by reference).

What is claimed is:

1. Apparatus for transcutaneously pacing a heart at a pacing rate, the apparatus comprising stimuli generating circuitry for generating electrical stimuli at an output, and electrodes connected to the output of the stimuli generating circuitry and adapted for delivering the electrical stimuli to a patient's chest, wherein said electrical stimuli include pacing stimuli delivered at the pacing rate, each pacing stimulus comprising a series of individual pulses, wherein each series of pulses has a duration and amplitude making it capable, as a group, of causing a contraction of the heart, but each individual pulse has a duration and amplitude making it incapable, by itself, of causing such a contraction.

2. Apparatus for transcutaneously pacing a heart at a pacing rate, the apparatus comprising stimuli generating circuitry for generating electrical stimuli at an output, and electrodes connected to the output of the stimuli generating circuitry and adapted for delivering the electrical stimuli to a patient's chest, wherein said electrical stimuli include pacing stimuli delivered at the pacing rate, each pacing stimulus comprising a series of individual pulses, wherein said series of pulses extends for a duration of at least 5 msec.

3. Apparatus for transcutaneously pacing a heart at a pacing rate, the apparatus comprising stimuli generating circuitry for generating electrical stimuli at an output, and electrodes connected to the output of the stimuli generating circuitry and adapted for delivering the electrical stimuli to a patients's chest, wherein said electrical stimuli include pacing stimuli delivered at the pacing rate, each pacing stimulus comprising a series of individual pulses, wherein the duration of the individual pacing pulses averages less than 0.5 msec.

4. The apparatus of claim 3 wherein said average pulse duration is less than 250 microseconds.

5. The apparatus of claim 4 wherein said average pulse duration is less than 50 microseconds.

6. The apparatus of either of claims 3, 4, or 5 wherein the duty cycle of said individual pulses is greater than 20%.

7. The apparatus of claim 6 wherein the duty cycle of said individual pulses is greater than 50%.

8. The apparatus of claim 6 wherein the average amplitudes of said series of individual pacing pulses rise from a first amplitude to a second amplitude.

9. The apparatus of claim 8 wherein said first amplitude is less than the threshold for stimulation of skeletal muscle.

10. The apparatus of claim 9 wherein said second amplitude is reached in not less than 2 pulses.

11. Apparatus for transcutaneously pacing a heart at a pacing rate, the apparatus comprising
   stimuli generating circuitry for generating electrical stimuli at an output, and
   electrodes connected to the output of the stimuli generating circuitry and adapted for delivering the electrical stimuli to a patient's chest,
   wherein said electrical stimuli include pacing stimuli delivered at the pacing rate, each pacing stimulus comprising a series of individual pulses,
   wherein the amplitude of said pacing stimulus in the interval between individual pulses is less than the threshold amplitude for stimulating cardiac muscle.

12. Apparatus for transcutaneously pacing a heart at a pacing rate, the apparatus comprising
   stimuli generating circuitry for generating electrical stimuli at an output, and
   electrodes connected to the output of the stimuli generating circuitry and adapted for delivering the electrical stimuli to a patient's chest,
   wherein said electrical stimuli include pacing stimuli delivered at the pacing rate, each pacing stimulus comprising a plurality of pulses, with at least the initial pulse in each stimulus having an amplitude less than the threshold for causing contractions of skeletal muscle and cardiac muscle, and subsequent pulses have amplitudes greater than said threshold.

13. The apparatus of claim 12 wherein each succeeding initial pulse has a generally greater amplitude than the preceding pulses.

14. Apparatus for transcutaneously pacing a heart at a pacing rate, the apparatus comprising
   stimuli generating circuitry for generating electrical stimuli at an output, and
   electrodes connected to the output of the stimuli generating circuitry and adapted for delivering the electrical stimuli to a patient's chest,
   wherein said electrical stimuli include pacing stimuli delivered at the pacing rate, each pacing stimulus comprising a series of individual pulses,
   wherein the series of individual pulses is such that, at cardiac threshold (i.e., when the pacing stimuli are adjusted to an amplitude just high enough to cause cardiac contractions), there is less skeletal muscle stimulation than would result using a continuous pulse having the same duration as the series of pulses.

15. Apparatus for transcutaneously pacing a heart at a pacing rate, the apparatus comprising
   stimuli generating circuitry for generating electrical stimuli at an output, and
   electrodes connected to the output of the stimuli generating circuitry and adapted for delivering the electrical stimuli to a patient'chest,
   wherein said electrical stimuli include pacing stimuli delivered at the pacing rate, each pacing stimulus comprising a series of individual pulses,
   wherein the series of individual pulses is such that, at cardiac threshold (i.e., when the pacing stimuli are adjusted to an amplitude just high enough to cause cardiac contractions), there is less discomfort to the patient than would result using a continuous pulse having the same duration as the series of pulses.

16. A method of transcutaneously pacing a heart at a pacing rate, the method comprising the steps of:
   generating electrical pacing stimuli;
   delivering the stimuli to a patient through electrodes applied to the patient's chest;
   wherein the pacing stimuli generated and delivered to the patient comprise a series of individual pulses,
   wherein each series of pulses has a duration and amplitude making it capable, as a group, of causing a contraction of the heart, but each individual pulse has a duration and amplitude making it incapable, by itself, of causing such a contraction.

17. A method of transcutaneously pacing a heart at a pacing rate, the method comprising the steps of:
   generating electrical pacing stimuli;
   delivering the stimuli to a patient through electrodes applied to the patient's chest;
   wherein the pacing stimuli generated and delivered to the patient comprise a series of individual pulses,
   wherein said series of pulses extends for a duration of at least 5 msec.

18. A method of transcutaneously pacing a heart at a pacing rate, the method comprising the steps of:
   generating electrical pacing stimuli;
   delivering the stimuli to a patient through electrodes applied to the patient's chest;
   wherein the pacing stimuli generated and delivered to the patient comprise a series of individual pulses,
   wherein the duration of the individual pacing pulses averages less than 0.5 msec.

19. The method of claim 18 wherein said average pulse duration is less than 250 microseconds.

20. The method of claim 19 wherein said average pulse duration is less than 50 microseconds.

21. The method of either of claim s 18, 19, or 20 wherein the duty cycle of said individual pulses is greater than 20%.

22. The method of claim 21 wherein the duty cycle of said individual pulses is greater than 50%.

23. The method of claim 21 wherein the average amplitudes of said series of individual pulses rise from a first amplitude to a second amplitude.

24. The method of claim 23 wherein said first amplitude is less than the threshold for stimulation of skeletal muscle.

25. The method of claim 24 wherein said second amplitude is reached in not less than 2 pulses.

26. A method of transcutaneously pacing a heart at a pacing rate, the method comprising the steps of:
   generating electrical pacing stimuli;
   delivering the stimuli to a patient through electrodes applied to the patient's chest;
   wherein the pacing stimuli generated and delivered to the patient comprise a series of individual pulses,
   wherein the amplitude of said pacing stimulus in the interval between individual pulses is less than the pulse amplitude required for stimulating cardiac muscle if the pulse amplitude remained constant for the duration of the series of pulses.

27. A method of transcutaneously pacing a heart at a pacing rate, the method comprising the steps of:
   generating electrical pacing stimuli;
   delivering the stimuli to a patient through electrodes applied to the patient's chest;
   wherein the pacing stimuli generated and delivered to the patient comprise a plurality of pulses, with at least the initial pulse in each stimulus having an amplitude less than the threshold for causing contractions of skeletal muscle and cardiac muscle, and subsequent pulses have amplitudes greater than said threshold.

28. The method of claim 27 wherein each succeeding initial pulse has a generally greater amplitude than the preceding pulses.

29. A method of transcutaneously pacing a heart at a pacing rate, the method comprising the steps of:
generating electrical pacing stimuli;
delivering the stimuli to a patient through electrodes applied to the patient's chest;
wherein the pacing stimuli generated and delivered to the patient comprise a series of individual pulses,
wherein the series of individual pulses is such that, at cardiac threshold (i.e. when the pacing stimuli are adjusted to an amplitude just high enough to cause cardiac contractions), there is less skeletal muscle stimulation than would result using a continuous pulse having the same duration as the series of pulses.

30. A method of transcutaneously pacing a heart at a pacing rate, the method comprising the steps of:
generating electrical pacing stimuli;
delivering the stimuli to a patient through electrodes applied to the patient's chest;
wherein the pacing stimuli generated and delivered to the patient comprise a series of individual pulses,
wherein the series of individual pulses is such that, at cardiac threshold (i.e. when the pacing stimuli are adjusted to an amplitude just high enough to cause cardiac contractions), there is less discomfort to the patient than would result using a continuous pulse having the same duration as the series of pulses.

* * * * *